(12) United States Patent
Henderson (10) Patent No.: US 7,857,843 B2
(45) Date of Patent: Dec. 28, 2010

(54) DIFFERENTIALLY EXPANDED VASCULAR GRAFT

(75) Inventor: Jamie Henderson, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1069 days.

(21) Appl. No.: 11/026,777

(22) Filed: Dec. 31, 2004

(65) Prior Publication Data

US 2006/0155371 A1 Jul. 13, 2006

(51) Int. Cl.
*A61F 2/06* (2006.01)

(52) U.S. Cl. .................................................. 623/1.4

(58) Field of Classification Search ................ 623/1.39, 623/1.4, 1.49, 1.54, 921, 1.32, 23.71, 23.76
See application file for complete search history.

(56) References Cited

U.S. PATENT DOCUMENTS

| | | | |
|---|---|---|---|
| 3,640,984 A | 2/1972 | Miller | |
| 3,664,915 A | 5/1972 | Gore | |
| 3,953,566 A | 4/1976 | Gore | |
| 3,962,153 A | 6/1976 | Gore | |
| 4,096,227 A | 6/1978 | Gore | |
| 4,101,984 A | 7/1978 | MacGregor | |
| 4,187,390 A | 2/1980 | Gore | |
| 4,208,745 A * | 6/1980 | Okita | 623/1.4 |
| 4,281,669 A | 8/1981 | MacGregor | |
| 4,304,010 A | 12/1981 | Mano | |
| 4,355,426 A | 10/1982 | MacGregor | |
| 4,454,249 A | 6/1984 | Suzuki et al. | |
| 4,459,252 A | 7/1984 | MacGregor | |
| 4,576,608 A | 3/1986 | Homsy | |
| 4,627,836 A | 12/1986 | MacGregor | |
| 4,647,416 A | 3/1987 | Seiler, Jr. et al. | |
| 4,713,070 A * | 12/1987 | Mano | 623/1.39 |
| 4,743,480 A | 5/1988 | Campbell et al. | |
| 4,816,339 A | 3/1989 | Tu et al. | |
| 4,822,341 A | 4/1989 | Colone | |
| 4,849,285 A | 7/1989 | Dillon | |
| 4,902,423 A | 2/1990 | Bacino | |
| 4,957,669 A | 9/1990 | Primm | |
| 4,973,609 A | 11/1990 | Browne | |

(Continued)

FOREIGN PATENT DOCUMENTS

CA 1069252 1/1980

(Continued)

OTHER PUBLICATIONS

Machine translation of JP 5-84292 A.*

(Continued)

*Primary Examiner*—David H. Willse
(74) *Attorney, Agent, or Firm*—Vidas, Arrett & Steinkraus P.A.

(57) ABSTRACT

A differentially expanded vascular graft for implantation within a body includes a PTFE tube formed of a homogeneous material. The PTFE tube has a longitudinal first portion which has been longitudinally expanded, and a longitudinal second portion which has been longitudinally expanded. The first and second portions have respective microstructures which are different from one another. A method and apparatus for making the differentially expanded vascular graft of the present invention facilitates the formation of the various expanded portions of the PTFE tube.

4 Claims, 5 Drawing Sheets

U.S. PATENT DOCUMENTS

| | | | |
|---|---|---|---|
| 4,975,669 A | 12/1990 | Wojtowicz | |
| 5,024,671 A | 6/1991 | Tu et al. | |
| 5,071,609 A | 12/1991 | Tu et al. | |
| 5,141,522 A | 8/1992 | Landi | |
| 5,192,310 A | 3/1993 | Herweck et al. | |
| 5,207,960 A | 5/1993 | Moret de Rocheprise | |
| 5,326,355 A | 7/1994 | Landi | |
| 5,433,909 A | 7/1995 | Martakos et al. | |
| 5,449,373 A | 9/1995 | Pinchasik et al. | |
| 5,462,781 A | 10/1995 | Zukowski | |
| 5,607,478 A | 3/1997 | Lentz et al. | |
| 5,609,624 A | 3/1997 | Kalis | |
| 5,620,763 A | 4/1997 | House et al. | |
| 5,628,786 A | 5/1997 | Banas et al. | |
| 5,641,373 A | 6/1997 | Shannon et al. | |
| 5,643,309 A | 7/1997 | Myler et al. | |
| 5,716,660 A | 2/1998 | Weadock et al. | |
| 5,718,973 A | 2/1998 | Lewis et al. | |
| 5,733,303 A | 3/1998 | Israel et al. | |
| 5,735,892 A | 4/1998 | Myers et al. | |
| 5,747,128 A | 5/1998 | Campbell et al. | |
| 5,749,880 A | 5/1998 | Banas et al. | |
| 5,800,512 A | 9/1998 | Lentz et al. | |
| 5,810,870 A | 9/1998 | Myers et al. | |
| 5,824,042 A | 10/1998 | Lombardi et al. | |
| 5,824,050 A | 10/1998 | Karwoski et al. | |
| 5,840,775 A | 11/1998 | Howard, Jr. et al. | |
| 5,843,171 A | 12/1998 | Campbell et al. | |
| 5,843,173 A | 12/1998 | Shannon et al. | |
| 5,858,556 A | 1/1999 | Eckert et al. | |
| 5,861,033 A | 1/1999 | Martakos et al. | |
| 5,897,587 A | 4/1999 | Martakos et al. | |
| 5,925,075 A | 7/1999 | Myers et al. | |
| 5,928,279 A | 7/1999 | Shannon et al. | |
| 5,972,018 A | 10/1999 | Israel et al. | |
| 5,976,192 A | 11/1999 | McIntyre et al. | |
| 5,980,799 A | 11/1999 | Martakos et al. | |
| 6,001,125 A | 12/1999 | Golds et al. | |
| 6,004,348 A | 12/1999 | Banas et al. | |
| 6,010,529 A | 1/2000 | Herweck et al. | |
| 6,016,848 A | 1/2000 | Egres | |
| 6,039,755 A | 3/2000 | Banas et al. | |
| 6,048,360 A | 4/2000 | Khosravi et al. | |
| 6,048,484 A | 4/2000 | House et al. | |
| 6,053,943 A | 4/2000 | Edwin et al. | |
| 6,080,198 A | 6/2000 | Lentz et al. | |
| 6,124,523 A | 9/2000 | Banas et al. | |
| 6,132,457 A | 10/2000 | Chobotov | |
| 6,146,414 A | 11/2000 | Gelman | |
| 6,187,054 B1 | 2/2001 | Colone et al. | |
| 6,203,735 B1 | 3/2001 | Edwin et al. | |
| 6,214,039 B1 | 4/2001 | Banas et al. | |
| 6,231,598 B1 | 5/2001 | Berry et al. | |
| 6,245,101 B1 | 6/2001 | Drasler et al. | |
| 6,264,684 B1 | 7/2001 | Banas et al. | |
| 6,267,834 B1 | 7/2001 | Shannon et al. | |
| 6,283,991 B1 | 9/2001 | Cox et al. | |
| 6,287,337 B1 | 9/2001 | Martakos et al. | |
| 6,306,162 B1 | 10/2001 | Patel | |
| 6,319,279 B1 | 11/2001 | Shannon et al. | |
| 6,334,867 B1 | 1/2002 | Anson | |
| 6,355,063 B1 | 3/2002 | Calcote | |
| 6,364,900 B1 | 4/2002 | Heuser | |
| 6,371,981 B1 | 4/2002 | Yang et al. | |
| 6,383,214 B1 | 5/2002 | Banas et al. | |
| 6,402,779 B1 | 6/2002 | Colone et al. | |
| 6,416,537 B1 | 7/2002 | Martakos et al. | |
| 6,428,571 B1 | 8/2002 | Lentz et al. | |
| 6,443,981 B1 | 9/2002 | Colone et al. | |
| 6,451,047 B2 | 9/2002 | McCrea et al. | |
| 6,464,720 B2 | 10/2002 | Boatman et al. | |
| 6,488,701 B1 | 12/2002 | Nolting et al. | |
| 6,579,314 B1 | 6/2003 | Lombardi et al. | |
| 6,582,463 B1 | 6/2003 | Mowry et al. | |
| 6,605,119 B1 | 8/2003 | Colone et al. | |
| 6,699,276 B2 | 3/2004 | Sogard et al. | |
| 6,719,783 B2 | 4/2004 | Lentz et al. | |
| 6,758,858 B2 | 7/2004 | McCrea et al. | |
| 6,786,920 B2 | 9/2004 | Shannon et al. | |
| 6,790,225 B1 | 9/2004 | Shannon et al. | |
| 6,797,217 B2 | 9/2004 | McCrea et al. | |
| 6,805,706 B2 | 10/2004 | Solovay et al. | |
| 6,994,723 B1 | 2/2006 | McMahon | |
| 7,011,682 B2 | 3/2006 | Lashinski et al. | |
| 7,090,693 B1 | 8/2006 | Chobotov et al. | |
| 2001/0020181 A1 | 9/2001 | Layne | |
| 2001/0021870 A1 | 9/2001 | Edwin et al. | |
| 2001/0025131 A1 | 9/2001 | Edwin et al. | |
| 2002/0026231 A1 | 2/2002 | Shannon | |
| 2002/0042645 A1 | 4/2002 | Shannon | |
| 2002/0052649 A1 | 5/2002 | Greenhalgh | |
| 2002/0111667 A1 | 8/2002 | Girton et al. | |
| 2002/0115986 A1 | 8/2002 | Shadduck | |
| 2002/0198588 A1 | 12/2002 | Armstrong et al. | |
| 2003/0017775 A1 | 1/2003 | Sowinski et al. | |
| 2003/0028240 A1 | 2/2003 | Nolting et al. | |
| 2003/0135265 A1 | 7/2003 | Stinson | |
| 2003/0135266 A1 | 7/2003 | Chew et al. | |
| 2003/0144725 A1 | 7/2003 | Lombardi | |
| 2003/0191519 A1 | 10/2003 | Lombardi et al. | |
| 2003/0211258 A1 | 11/2003 | Srinivasan et al. | |
| 2004/0106975 A1 | 6/2004 | Solovay et al. | |
| 2005/0027347 A1 | 2/2005 | Chobotov et al. | |
| 2005/0283220 A1* | 12/2005 | Gobran et al. | 623/1.4 |
| 2006/0149361 A1 | 7/2006 | Henderson et al. | |
| 2006/0149366 A1 | 7/2006 | Henderson | |
| 2007/0088368 A1 | 4/2007 | Acosta et al. | |

FOREIGN PATENT DOCUMENTS

| | | |
|---|---|---|
| GB | 1506432 | 4/1978 |
| GB | 0003387 | 2/2000 |
| JP | 59 062124 | 4/1984 |
| JP | 5-84292 A * | 4/1993 |
| SU | 468796 | 4/1975 |
| WO | WO 96/00103 | 1/1996 |
| WO | 9806355 | 2/1998 |
| WO | WO 98/26731 | 6/1998 |
| WO | WO 00/43051 | 7/2000 |

OTHER PUBLICATIONS

PCT Notification of Transmittal of the International Search Report and the Written Opinion of the International Searching Authority, or the Declaration for International Application No. PCT/US2005/047206, May 17, 2006 (2 pages).

PCT International Search Report for International Application No. PCT/US2005/047206, May 17, 2006 (5 pages).

PCT Written Opinion for International Application No. PCT/US2005/047206, May 17, 2006, 9 pages.

* cited by examiner

DIFFERENTIALLY EXPANDED VASCULAR GRAFT

FIELD OF THE INVENTION

The present invention relates generally to a vascular graft formed of polytetrafluoroethylene (PTFE). More specifically, the present invention relates to such a vascular graft having longitudinally expanded portions distributed longitudinally along the graft, where the longitudinal expansion of the portions differs such that the microstructure of the graft varies longitudinally along the length thereof. Also, the present invention relates to a method and apparatus for making the vascular graft.

BACKGROUND OF THE INVENTION

It is well known to use extruded tubes of polytetrafluoroethylene (PTFE) as implantable intraluminal prostheses, particularly vascular grafts. PTFE is particularly suitable as an implantable prosthesis as it exhibits superior biocompatibility. PTFE tubes may be used as vascular grafts in the replacement or repair of a blood vessel as PTFE exhibits low thrombogenicity. In vascular applications, the grafts are manufactured from expanded polytetrafluoroethylene (ePTFE) tubes. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). A graft having a large IND may enhance tissue ingrowth and cell endothelization by a significant portion of the graft having interior voids some of which provide passages through the tube wall between the outer and inner surfaces thereof. This provides the graft with porosity.

Microporous ePTFE tubes for use as vascular grafts are known. The porosity of an ePTFE vascular graft may be controllably varied by controllably varying the IND. For example, an increase in the ND within a given structure may result in an increased porosity, i.e., increased pore size, by increasing the distance between nodes resulting in thinning of the fibrils. This, in turn, results in larger voids, i.e., pores, in the ePTFE material. Increased porosity typically enhances tissue ingrowth as well as cell endothelization along the inner and outer surface of the ePTFE tube.

Increasing the porosity of an ePTFE tube, however, may limit other properties of the tube. For example, increasing the porosity of the tube may reduce the overall radial and tensile strength thereof as well as reduce the ability of the graft to retain a suture placed in the tube during implantation. Such a suture typically extends through the wall of the graft. Also, such microporous tubes tend to exhibit low axial tear strength, so that a small tear or nick will tend to propagate along the length of the tube. Thus, if the ePTFE tube has a uniform porosity along its length, the degree of porosity of therein may be limited by the strength requirements of the tube.

Alternatively, if the strength requirements for the PTFE tube may be satisfied by selected longitudinal sections of the tube having the required strength, then it may be possible for other longitudinal sections of the tube to have an elevated porosity, even if such other longitudinal sections have limited strength. For example, it may be desirable for selected axial portions of the ePTFE tube to have sufficient stiffness to prevent kinking. Such stiffness may be provided by increasing the stiffness of such axial portions where such axial portions have an annular cross-section and accordingly, the shape of individual rings. Such axial portions may typically be spaced apart from one another longitudinally and nevertheless provide the necessary stiffness to the vascular graft. Therefore, the portions of the graft between stiffened axial portions may have a lower requirement for strength and may therefore have a higher porosity.

Another example of one or more selected axial portions of a vascular graft having increased requirements for strength is where such one or more portions are to be pierced for insertion of a suture therethrough. If the portion of the graft to be pierced can be identified just prior to the piercing, then other longitudinal sections of the graft may have lower strength requirements and therefore have a higher porosity.

Another possible technique for increasing the radial tensile and axial tear strength of microporous ePTFE tubes is to modify the structure of the extruded PTFE tubing during formation so that the resulting expanded tube has non-longitudinally aligned fibrils. Forming an expanded PTFE tube with non-longitudinally aligned fibrils is typically difficult as it may require extrusion of the tube using complex equipment before expansion of the tube. Other possible methods for forming non-longitudinally aligned fibrils would be expected to be complex.

Additional properties, which may or may not be related to porosity and strength, may be desirably varied along the length of a ePTFE tube. For example, it may be desirable for the density of the tube to vary for different longitudinal positions on the tube. Density may be related to porosity, e.g., inversely proportional thereto, since the greater the voids in a selected section of the ePTFE tube, the lower the weight of the section.

Another property of an ePTFE tube which may desirably be varied along the length thereof is the number and thickness of the fibrils connecting individual nodes. This property may also be related to porosity because increasing the number and thickness of such fibrils may reduce the size of the voids in the ePTFE tube and thereby reduce the porosity thereof. Accordingly, if the number and thickness of fibrils is not reduced by an increase in the IND, then such an increase may not result in an increased porosity of the ePTFE tube.

A further property of an ePTFE tube which may be desirably varied along the length thereof is the length of the fibrils connecting individual nodes. Increasing the length of the fibrils increases the flexibility of the ePTFE tube, even if the number and thickness of the fibrils is not changed.

A possible technique for varying the properties of an ePTFE along the length thereof may include longitudinally expanding the entire tube and then longitudinally compressing selected axial portions thereof. Such longitudinal compression typically results in a decrease in the IND, and decreased porosity in the compressed axial portions. Also, such longitudinal compression typically results in bending or folding of the fibrils. Also, the microstructure resulting therefrom differs significantly from the node and fibril microstructure which would be caused by longitudinal expansion of the axial portion to the same axial dimension as results from the longitudinal compression.

SUMMARY OF THE INVENTION

The differentially expanded vascular graft of the present invention is for implantation within a body. The vascular graft includes a PTFE tube formed of a homogeneous material. The PTFE tube has a longitudinal first portion which has been longitudinally expanded, and a longitudinal second portion which has been longitudinally expanded. The first and second portions have respective microstructures which are different from one another. A method and apparatus for making the differentially expanded vascular graft of the present invention facilitates the formation of the various expanded portions of the PTFE tube.

One of the characteristics of the microstructures of the first and second portions which may be different are the respective INDs for the portions. This, in turn, typically results in other properties of the first and second portions being different, such as porosity, permeability, density or strength. This enables the formation of a vascular graft selected portions of which have respective properties, the combination of which may be difficult to provide in a single graft made according to conventional techniques. Thus, for example, a single graft of the present invention may have some portions with high porosity and other portions with low porosity.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
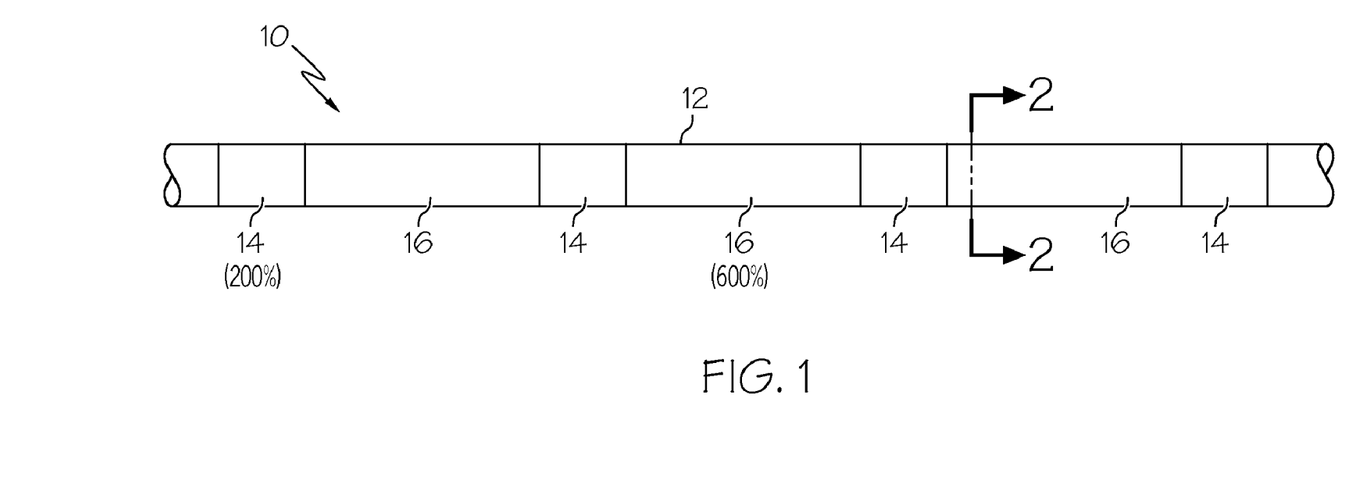
FIG. 1 is a side elevational view of the differentially expanded vascular graft of the present invention, the graft having annular portions which have been expanded longitudinally by different amounts.
Figure 2:
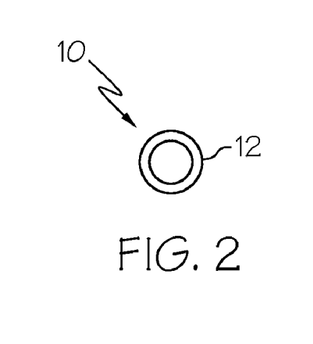
FIG. 2 is a longitudinal cross-sectional view of the differentially expanded vascular graft of FIG. 1 in the plane indicated by line 3-3 of FIG. 1.

Referring to the drawings and more particularly to FIGS. 1 and 2, a differentially expanded vascular graft 10 is shown for implantation within a body. The vascular graft 10 includes a PTFE tube 12 formed of homogeneous material. The tube 12 has longitudinal first and second portions 14, 16 in alternating relation as shown in FIG. 1. The first and second portions 14, 16 have been longitudinally expanded by different amounts. For example, in the embodiment of FIG. 1, the first portions 14 have each been longitudinally expanded such that the lengths thereof increase by 200%. The second portions 16 have each been longitudinally expanded such that the lengths thereof increase by 600%. The respective amounts of the expansion of the first and second portions 14, 16 result in the PTFE material of the first portions 14 having generally the same microstructures and the PTFE material of the second portions 16 having generally the same microstructure. Further, the different amounts of expansion result in the microstructures of the first portions 14 being different from the microstructures of the second portions 16. The microstructures of the first and second portions 14, 16 may be locked by sintering thereof.

The first and second portions 14, 16 of the PTFE tube 12 each have annular cross-sections such that each portion has a ring-shape, as shown in FIG. 2. The respective outer and inner diameters of each of the portions 14, 16 are the same. The respective lengths of the portions 14, 16 are different. The respective longitudinal expansions which provide the lengths of the portions 14, 16 may constitute the complete longitudinal expansion of the PTFE tube 12 such that the length thereof after the respective longitudinal expansions is the target length.

In alternative embodiments of the vascular graft 10, the first and second portions 14, 16 may be expanded by amounts other than the 200% and 600% of FIG. 1. Also, the PTFE tube 12 may have additional longitudinal portions which are expanded by further differing amounts.

Figure 3:
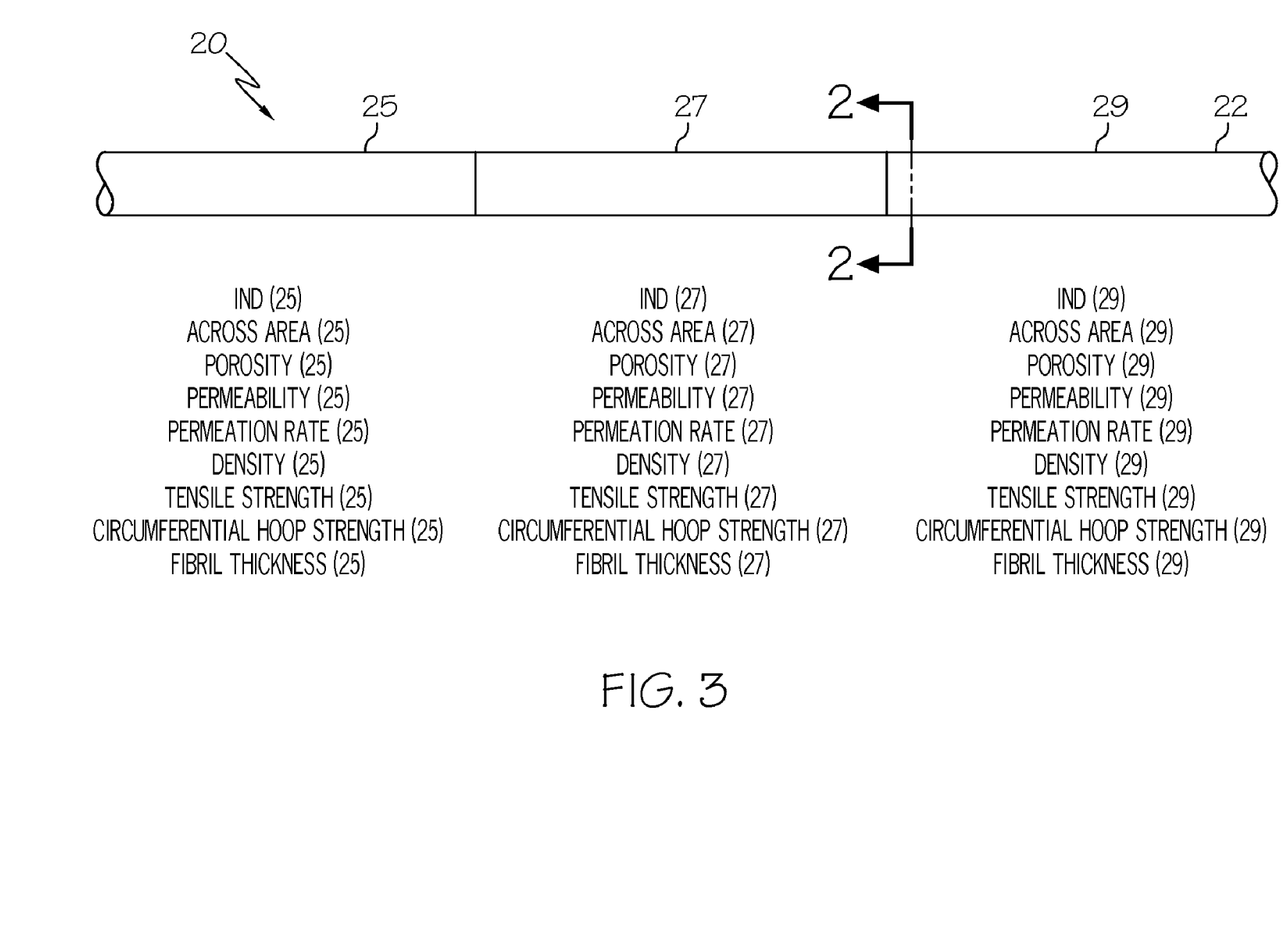
FIG. 3 is a generalized schematic view of an alternative embodiment of the differentially expanded vascular graft of FIG. 1, the graft having annular expanded portions which have different microstructures.

A generalized schematic view of an alternative embodiment of the vascular graft 20 is shown in FIG. 3. The vascular graft 20 includes a PTFE tube 22 formed of homogeneous material and having longitudinal first, second, and third portions 25, 27, 29 which have different microstructures. While the microstructures differ, the chemical composition of the portions 25, 27, 29 are the same thereby making the material of the PTFE tube 22 homogeneous. The different microstructures of the portions 25, 27, 29 result from respective longitudinal expansions thereof. The desired microstructures of the portions 25, 27, 29 of the PTFE tube 22 may be locked by sintering thereof.

The different microstructures of the portions 25, 27, 29 of the PTFE tube 22 each have a fibrous state which is defined by interspaced nodes which are interconnected by elongated fibrils, referred to herein as a "node and fibril microstructure". The distance between adjacent nodes which is spanned by the fibrils is defined as the internodal distance (IND). The microstructures of the portions 25, 27, 29 each have corresponding INDs which differ according to the differences in the respective microstructures. The INDs for the corresponding portions 25, 27, 29 are indicated by the suffixes (25), (27), (29) in FIG. 3.

The node and fibril microstructure includes spaces between the outer surfaces of the nodes and fibers which provide the microstructure with pores. Typically, these pores result in porosity which typically increases with increasing IND (25), (27), (29) because a large IND normally provides greater flexibility of fibers to increase porosity. It is possible to have a relatively larger IND (25), (27), (29) with a relatively large number or thickness of fibrils between the nodes. This would also increase the length of the fibrils which would result in greater flexibility thereof and increased porosity.

The microstructures of the portions 25, 27, 29 each have corresponding pore sizes which differ according to the differences in the respective microstructures. The pore sizes may be indicated by across areas which are the areas of the pores included in defined areas of a plane which is perpendicular to a radius of the PTFE tube 22. The respective across areas for the portions 25, 27, 29 therefore differ from one another according to the differences in pore sizes. The across areas for the corresponding portions 25, 27, 29 are indicated by the suffixes (25), (27), (29) in FIG. 3.

Alternatively, the respective node and fibril microstructures may differ by the size and shape of the nodes. Typically, a microstructure having large nodes has fewer fibrils and a microstructure having small nodes has more fibrils. Expansion of the PTFE tube 22 normally produces nodes which are smaller because material is transferred therefrom to the fibrils to provide increased length of the fibrils. Typically, the thickness of the fibrils remains generally constant during such expansion. Expansion of PTFE, such as by 200%, may produce microstructures having small or large nodes, long or short fibrils, and different numbers of fibrils and nodes, such that these characteristics of the microstructure are normally independent of the expansion percentage.

Also, nodes which are relatively large normally limit the size of the pores since the relatively large nodes limit the space available in the tube wall for the pores. Conversely, relatively small nodes typically result in increased pore sizes. The shape of the nodes may affect the microstructure, such as by providing an external surface which affects the connection of the fibrils to the nodes. For example, nodes having a relatively large, uniform outer surface area may facilitate connection of the fibrils thereto, including the connection of large numbers of fibrils or fibrils having a relatively large thickness. Also, the shape of the nodes may be sufficiently uniform to enable the extension of fibrils therefrom in various directions.

Groups of the pores within the node and fibril microstructure of the PTFE tube 22 are typically interconnected to provide passageways, which are typically tortuous and partially non-radial, through the respective tube walls of the portions 25, 27, 29 between the inner and outer surfaces thereof. This provides the portions 25, 27, 29 with respective porosities and permeabilities allowing gas and liquid to flow through the respective tube walls of the portions 25, 27, 29 between the inner and outer surfaces thereof. Such flow of gas or liquid typically occurs during test conditions when the pressure of the gas or liquid is elevated. During normal use of the PTFE tube 22 within the body of a patient, fluid does not flow through the walls of the portions 25, 27, 29. The porosities and permeabilities may be different for the respective portions 25, 27, 29 depending upon the resistance to gas and liquid flow through the respective tube walls. The porosities and permeabilities for the corresponding portions 25, 27, 29 are indicated by the suffixes (25), (27) (29) in FIG. 3.

The different permeabilities in the portions 25, 27, 29 result in the respective portions having different permeation rates, indicated by the suffixes (25), (27), (29) in FIG. 3. The permeation rates are the respective speeds with which a gas, such as air, or liquid flows through a corresponding wall of the portions 25, 27, 29. Using a liquid to measure the permeability of the portions 25, 27, 29 may result in the liquid directing forces against the portions which exceed the strength thereof. Using a gas to measure the permeability of the portions 25, 27, 29 normally results in the gas directing forces against the portions which are below the strength thereof.

The different node and fibril microstructures may also result in the portions 25, 27, 29 of the PTFE tube 22 having different densities. The densities of corresponding portions 25, 27, 29 are indicated by the suffixes (25), (27), (29) in FIG. 3. The density of the portions 25, 27, 29 is typically inversely related to the spaces between the nodes and fibrils. This results from spaces between the nodes and fibrils reducing the amount of PTFE material present in a specific portion of the PTFE tube 22.

The different node and fibril microstructures may also result in the portions 25, 27, 29 of the PTFE tube 22 having different tensile strengths, and different circumferential hoop strengths. These tensile strengths and circumferential hoop strengths for the corresponding portions 25, 27, 29 are indicated by the suffixes (25), (27), (29) in FIG. 3.

Typically, fast longitudinal expansion results in high tensile strength and slow longitudinal expansion results in low tensile strength. The strength of the PTFE tube 22 following longitudinal expansion thereof may also be related to porosity since high porosity may result in low strength of the PTFE tube because the pores or spaces therein do not contain material which may provide strength to the PTFE tube. Conversely, low porosity may result in high strength of the PTFE tube 22. Other aspects of the PTFE tube 22 which affect the strength thereof may be affected by the longitudinal expansion of the PTFE tube. For example, the direction of the expansion of the PTFE tube 22 may produce a node and fibril microstructure in which the fibrils thereof have a specific orientation such as longitudinal, radial or inclination therebetween which may have a corresponding effect on the tensile or circumferential hoop strength of the PTFE tube. The ability to expand the PTFE tube 22 in a radial direction may be limited, although such expansion may be produced in the PTFE tube 22 by supplying air having an elevated pressure to the internal region thereof. Biaxial expansion of the PTFE tube 22, such as contemporaneous longitudinal and radial expansion thereof, is possible by supplying air having an elevated pressure to the internal region of the PTFE tube 22 during the longitudinal expansion of the PTFE tube. It is normally required to hold the expansion of the PTFE tube 22 physically, such as by clamping the ends of the expanded portions, before the sintering thereof.

The differences in the node and fibril microstructures may include differences in the respective fibril thicknesses for the portion 25, 27, 29 of the PTFE tube 22. The fibril thicknesses are the total thicknesses of all of the fibrils connected between adjacent nodes of respective microstructures. The fibril thicknesses for the corresponding portions 25, 27, 29 are indicated by the suffixes (25), (27), (29) in FIG. 3. These differences may affect various properties of the respective node and fibril microstructures, including porosity, across area, permeability, density, and strength.

The portions 25, 27, 29 of the PTFE tube 22 each may have annular cross-sections such that each portion has a ring-shape. The respective outer and inner diameters of each of the portions 25, 27, 29 may each be the same. The respective lengths of the portions 25, 27, 29 may be substantially different. The respective longitudinal expansions which provide the lengths of the portions 25, 27, 29 may constitute the complete longitudinal expansion of the PTFE tube 22 such that the length thereof after the respective longitudinal expansions is the target length.

Figure 4:
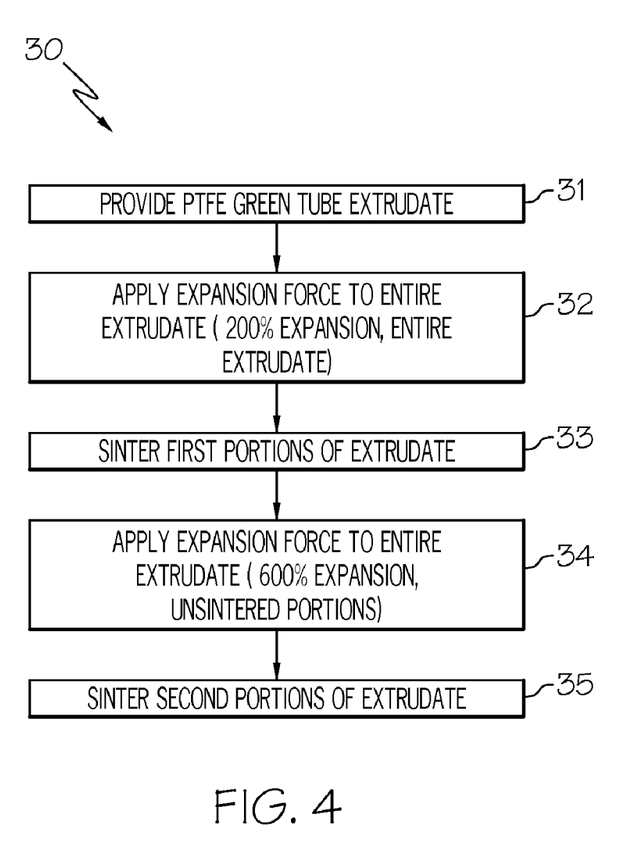
FIG. 4 is a block diagram showing a method for making a differentially expanded vascular graft of the present invention, the method including longitudinally expanding the respective portions of the vascular graft by different amounts.

A method 30 for making the first and second portions 14, 16 of the vascular graft 10 is represented by the block diagram of FIG. 4. The method 30 includes providing 31 an un-sintered PTFE green tube extrudate 12, including the first and second portions 14, 16, formed of homogeneous material. The homogeneous material of the PTFE tube 12 is provided by a material having a uniform chemical composition.

The method 30 further includes longitudinally expanding 32 the green tube extrudate 12, including all of the first and second portions 14, 16, such that the lengths of each of the first and second portions increases by 200%. The first portions 14 are each sintered 33 to lock the microstructures and prevent further expansion thereof.

The method 32 further includes longitudinally expanding 34 the green tube extrudate 12, including all of the first and second portions 14, 16, such that the lengths of each of the second portions increases by 600%. The sintering 33 of the first portions 14 prevents further expansion thereof such that the expansion 34 does not produce further significant expansion of the first portions. As a result, the expansion of the first portions 14 of 200% is not significantly changed by the expansion 34.

The method 32 includes sintering 35 the green tube extrudate 12, including all of the first and second portions 14, 16, to lock the microstructures of the second portions 16 and prevent further expansion thereof. Inclusion of the first portions 14 in the sintering 33 is not required since the microstructures of the first portions 14 were previously locked by the sintering 33. However, inclusion of the first portions 14 in the sintering 35 simplifies the performance thereof since sintering of the second portions 16, without sintering the first portions 14, is not required. This enables a single sintering process to be used contemporaneously for each of the first and second portions 14, 16, such as by heating the entire tube 12 in an oven.

Figure 5:
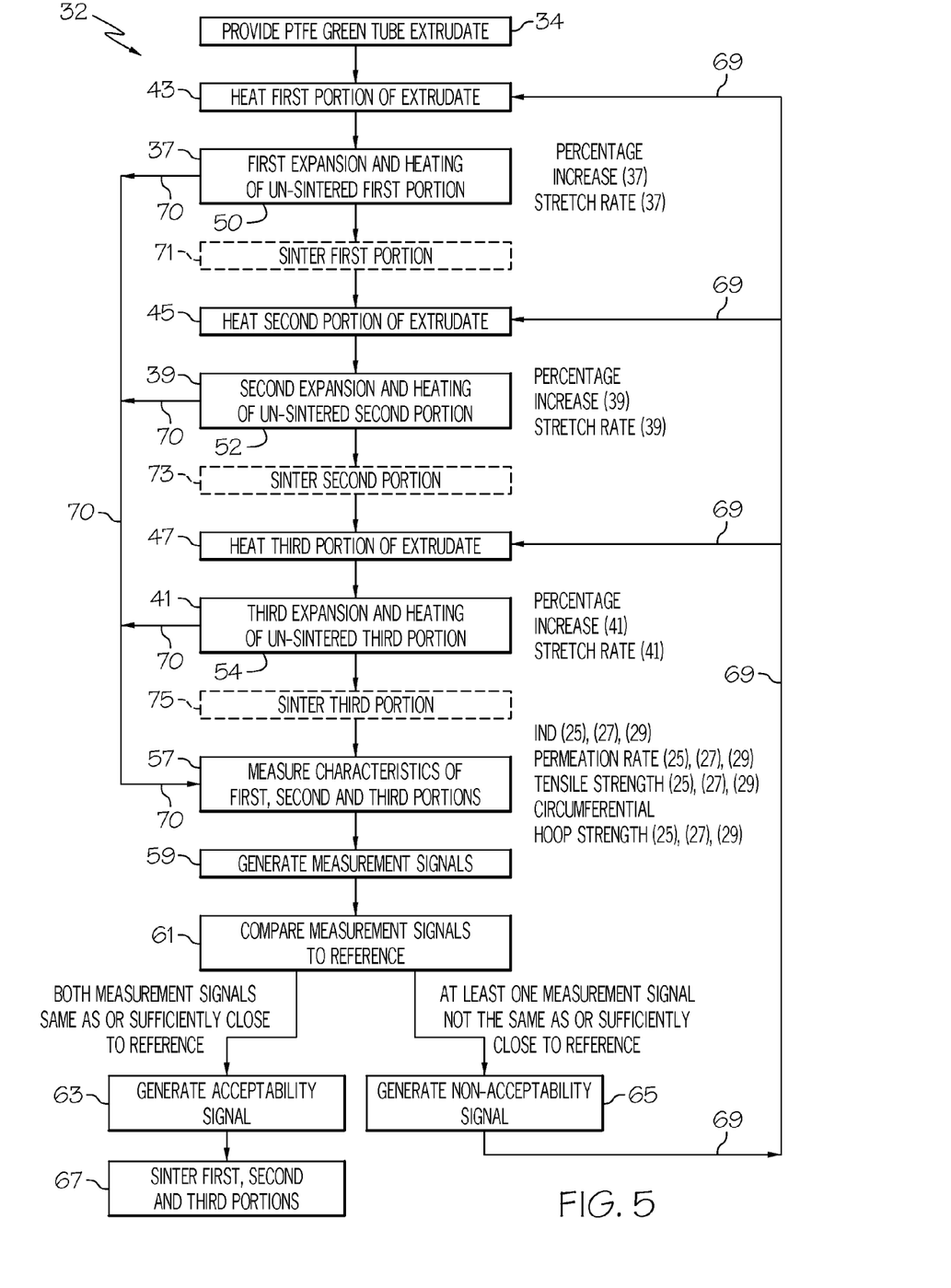
FIG. 5 is a block diagram showing an alternative method for making a differentially expanded vascular graft of FIG. 4, the method including expanding the respective portions of the vascular graft and verifying the corresponding microstructures of the portions.

The respective microstructures of the portions 25, 27, 29 may be produced according to the method 36 represented by the block diagram of FIG. 5. The method 36 includes providing 37 a PTFE tube 22, including the portions 25, 27, 29, formed of homogeneous material. The homogeneous material of the PTFE tube 22 is provided by a material having a uniform chemical composition. The provision 37 of the PTFE tube 22 may include the PTFE tube being an un-sintered green tube extrudate.

The method 36 further includes performing respective longitudinal expansions 38, 39, 41 of the portions 25, 27, 29 of the PTFE tube 22 to produce corresponding microstructures therein. The longitudinal expansions 38, 39, 41 produce respective microstructures in the portions 25, 27, 29 such that the microstructures are different.

The differences in the microstructures may be produced by the longitudinal expansions 38, 39, 41 producing different percentage increases of the corresponding portions 25, 27, 29 of the PTFE tube 22. The percentage increases produced by the corresponding longitudinal expansions 38, 39, 41 are indicated by the suffixes (38), (39), (41) in FIG. 5. The percentage increases (38), (39), (41) are the proportional increases in length of the portions 25, 27, 29 produced by the associated longitudinal expansions 38, 39, 41. The proportional increase is relative to the length of the respective portion 25, 27, 29 just before the associated longitudinal expansion 38, 39, 41.

The differences in the microstructures may result from longitudinally expanding 38, 39, 41 the portions 25, 27, 29 according to different stretch rates. The stretch rates of the respective longitudinal expansions 37, 39, 41 are indicated by the suffixes (38), (39), (41) in FIG. 5. The stretch rates (38), (39), (41) are the respective increases in the length of the portions 25, 27, 29 divided by the corresponding time periods during which the respective lengths are increased.

The longitudinal expansions 38, 39, 41 at different stretch rates (38), (39), (41) may result in different percentage increases (38), (39), (41) in the portions 25, 27, 29, or generally the same percentage increases. Such percentage increases (38), (39), (41) will be affected by the duration of the respective expansions 38, 39, 41 and the lengths of the portions 25, 27, 29 before the expansions.

The differences in the microstructures may be produced by heating 43, 45, 47 the portions 25, 27, 29 to different temperatures shortly before the respective expansions 38, 39, 41. This heating 43, 45, 47 of each of the portions 25, 27, 29 is timed to be before the corresponding expansions 38, 39, 41.

Also, the differences in the microstructures may be produced by heating 50, 52, 54 the portions 25, 27, 29 to different temperatures during the respective expansions 38, 39, 41. These temperatures applied to each of the portions 25, 27, 29 are timed to be during the corresponding expansions 38, 39, 41.

Additionally, the portions 25, 27, 29 may be heated both shortly before 43, 45, 47 and during 50, 52, 54 the respective expansions 38, 39, 41 to produce the different micro structures.

The method 36 further includes measuring 57 respective characteristics of the microstructures of the portions 25, 27, 29 which result from the respective expansions 38, 39, 41. This measuring 57 may be performed by a device which generates measurement signals 59 indicative of the respective measured characteristics. The device may provide a visual display based on the generation of the measurement signals 59 for direct viewing by a user who may determine therefrom whether the measured characteristics are the same as or sufficiently close to a reference indicative of acceptable microstructures. The user may alternatively determine, from viewing the visual display, that one or more of the measured characteristics are neither the same as nor sufficiently close to the reference to be acceptable.

Alternatively, the generation of the measurement signals 59 may provide electrical signals for transmission to an electronic processor, such as a microprocessor of a computer. Such an electronic processor may be programmed to compare the measurement signals to the reference 61 and generate an acceptability signal 63 for those measurement signals which are the same as or sufficiently close to the reference. The electronic processor may be further programmed to generate a non-acceptability signal 65 for those measurements signals which are neither the same as nor sufficiently close to the reference. The electronic processor is connected to a display device for receiving the acceptability or non-acceptability signals from the electronic processor and to communicate to the user whether the respective characteristics measured for the portions 25, 27, 29 are acceptable. If non-acceptability signals are generated 65, further expansions 38, 39, 41 and/or heating of the corresponding portions 25, 27, 29 to specific temperatures shortly before 43, 45, 47 and/or during 50, 52, 54 the expansions are possible to attempt to produce acceptable microstructures in the PTFE tube 22, as shown in FIG. 5.

One of the characteristics of the microstructures of the portions 25, 27, 29 which may be measured 57 are the respective INDs of the portions 25, 27, 29. The INDs measured in each of the portions 25, 27, 29 are indicated by the suffixes (25), (27), (29) in FIG. 5.

Alternative characteristics of the microstructures of the portions 25, 27, 29 which may be measured 57 are the respective permeation rates of the portions 25, 27, 29. The permeation rates measured in each of the portions 25, 27, 29 are indicated by the suffixes (25), (27), (29) in FIG. 5.

A further alternative characteristic of the microstructures of the portions 25, 27, 29 which may be measured 57 are the respective tensile strengths of the portions 25, 27, 29. The tensile strengths measured in each of the portions 25, 27, 29 are indicated by the suffixes (25), (27), (29) in FIG. 5.

A further alternative characteristic of the microstructures of the portions 25, 27, 29 which may be measured 57 are the respective circumferential hoop strengths of the portions 25, 27, 29. The circumferential hoop strengths measured in each of the portions 25, 27, 29 are indicated by the suffixes (25), (27), (29) in FIG. 5.

The method 36 includes sintering each of the portions 25, 27, 29 of the PTFE tube 22 following the corresponding expansions 38, 39, 41 thereof to lock the respective microstructures. It may be preferred for the sintering 67 to follow the determinations that the microstructures of the respective portions 25, 27, 29 are acceptable, such as by following the generation of the acceptability signals 63. This provides for the performance of further heating 43, 45, 47 and/or further expansions and heating 38, 39, 41 of one or more of the portions 25, 27, 29, if necessary, to produce acceptable microstructures therein before the sintering 79, 81, 83 thereof, as indicated by the reference numeral 69 in FIG. 5. Such further processing, such as by heating 43, 45, 47 and/or expansions and heating 38, 39, 41, may be followed by measurements of the characteristics 57 of the portions 25, 27, 29 on which such further processing was performed, as indicated by the reference numeral 70 in FIG. 5. Such measurements 57, and the subsequent comparisons to the reference 61, indicate whether acceptable microstructures in the portions 25, 27, 29 have been obtained or whether more of such further processing is required. This provides for possible iterations to produce acceptable microstructures which, once obtained, are then sintered 67 for locking thereof.

When the microstructures of each of the portions 25, 27, 29 is determined to be acceptable, such as by generation of corresponding acceptability signals 63, the sintering 67 is preferably performed as shortly thereafter as possible to lock the acceptable microstructures and prevent any unintended changes in the microstructures which, if sufficient, could result in the microstructures becoming unacceptable. For example, the microstructures may change after the expansions 38, 39, 41 and before the sintering 67 as a result of retraction of the portions 25, 27, 29. Such retraction may be prevented by forcibly retaining the portions 25, 27, 29 in their expanded dimension, such as by grasping the ends of the portions, after expansion, by clamps or retaining rings. Such grasping may, however, leave an imprint on the portions 25, 27, 29 which may be undesirable. The extent of such an imprint may be lessened by the sintering 67 being soon after the expansions 38, 39, 41.

It is also possible for the retraction to be limited by the contact between the portions 25, 27, 29 and the outer surface of the mandrel on which the PTFE tube 23 may be supported during the processing thereof. Such limitation of the retraction typically requires the contact between the PTFE tube 23 and the outer surface of the mandrel to prevent longitudinal translation of the PTFE tube relative thereto. Such prevention of longitudinal translation may be provided, for example, by the inner surface of the PTFE tube 23 being sticky.

Ordinarily, the PTFE tube 23 is required to be prevented from retraction by some type of restraint after expansion and before sintering 67. Otherwise, at least some retraction and resultant redistribution of the node and fibril microstructure may be expected.

Alternatively, it is possible for each of the portions 25, 27, 29 of the PTFE tube 22 to be sintered shortly after each of the corresponding expansions 38, 39, 41 and before the measurements 57 of the respective microstructures of the portions 25, 27, 29. Such sinterings are indicated by the reference numerals 71, 73, 75 and by broken lines to signify an alternative to the sintering 67. In this embodiment of the method, a PTFE tube 22 in which the microstructure is not acceptable in at least one of the portions 25, 27, 29 would likely be discarded since further alteration of such a microstructure for acceptability thereof, such as by further expansions 38, 39, 41 and/or heating 43, 45, 47, 50, 52, 54 of the portions 25, 27, 29, may be limited as a result of the sintering. Sintering before the measurements of the respective microstructures of the portions 25, 27, 29 may be advantageous, if acceptable microstructures therein are produced after the initial expansions 38, 39, 41 and/or heating 43, 45, 47, 50, 52, 54 of the portions 25, 27, 29, by reducing the opportunity for undesirable alteration of the microstructures which could possibly occur before or during the measurements of the microstructures 57 and associated determinations of the acceptability thereof 61, 63, 65.

As described in the foregoing, the method 36 may include performing different longitudinal expansions 38, 39, 41 on the respective portions 25, 27, 29 of the PTFE tube 22 to produce different microstructures therein. Alternatively, it is possible to perform the same expansions 38, 39, 41 on the respective portions 25, 27, 29 where the portions have different physical characteristics before the expansions to produce different microstructures in the portions 25, 27, 29 after the expansions. Differences in the physical characteristics of the portions 25, 27, 29 before the expansions 38, 39, 41 may be provided by different microstructures, which may be due to different INDs, or dimensions, such as the different thicknesses of the portions 25, 27, 29. Also, differences in the physical characteristics may be provided by pre-sintering sections of the portions 25, 27, 29, such as in the shape of circumferential rings or elongate longitudinal sections, before the expansions 38, 39, 41. Examples of such pre-sintering are disclosed in the U.S. Patent Application filed in the USPTO on even date herewith and titled "Sintered Ring Supported Vascular Graft", having as the inventors Jamie Henderson and Dennis Kujawski, and the application Ser. No. 11/026,748. Such differences in the physical characteristics of the portions 25, 27, 29 may be present in a PTFE tube 22 formed of homogeneous material since such a tube may have the same chemical composition while the portions 25, 27, 29 thereof differ in one or more of the physical characteristics.

Figure 6:
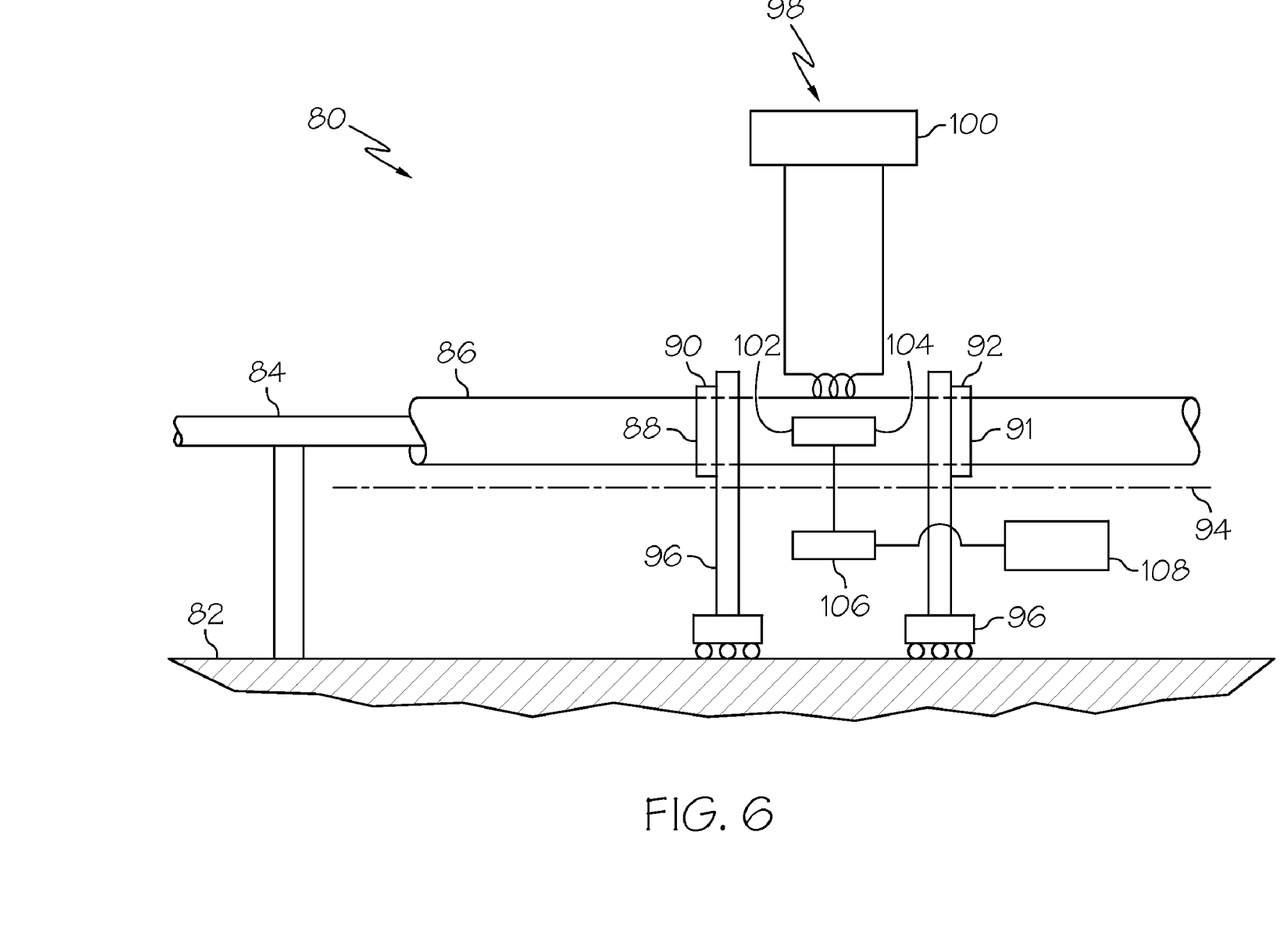
FIG. 6 is a schematic diagram showing an apparatus for making a differentially expanded vascular graft of the present invention, the apparatus including a pair of clamps for expanding an intermediate portion of the extrudate.

An apparatus 80 for making a differentially expanded vascular graft 20 is shown schematically in FIG. 6. The apparatus 80 includes a base 82 and a support fixture 84 mounted thereon. The support fixture 84 provides support for a PTFE tube 86, which may be a green tube extrudate. The support fixture 84 may include a mandrel on which the PTFE tube 86 may be supported.

The apparatus 80 further includes a first clamp 88 which is mounted on the base 82. The first clamp 88 is able to grip the PTFE tube 86 at a longitudinal first position 90 along the length thereof such that the first clamp is longitudinally fixed to the PTFE tube. The first position 90 is between the ends of the PTFE tube 86.

The apparatus 80 further includes a second clamp 91 mounted on the base 82. The second clamp 91 is able to grip a longitudinal second position 92 along the length of the PTFE tube 86 such that the second clamp is longitudinally fixed thereto. The second position 92 is between the ends of the PTFE tube 86.

The first and second clamps 88, 91 may be longitudinally displaced in opposite longitudinal directions 94 each of which is parallel to the longitudinal axis of the PTFE tube 86 when the PTFE tube is supported by the support fixture 84. Such longitudinal displacement of the first and second clamps 88, 91 increases the distance therebetween in the longitudinal direction 94.

The apparatus 80 provides for such displacement of the first and second clamps 88, 91 in the longitudinal directions 94 when the PTFE tube 86 is supported by the support fixture 84 and gripped between the first and second clamps. This results in longitudinal expansion of the portion of the PTFE tube 86 which is gripped between the first and second clamps 88, 91.

It is possible for the apparatus 80 to have either the first or second clamp 88, 91 fixed relative to the base 82 to prevent longitudinal displacement of the fixed one of the first and second clamps when the PTFE tube 86 is supported by the support fixture 84 and the PTFE tube is gripped by the first and second clamps. In such an apparatus 80, the other of the first or second clamps 88, 91 may be longitudinally displaced in the longitudinal direction 94 to increase the distance between the first and second clamps in the longitudinal direction. This results in the longitudinal expansion of the portion of the PTFE tube 86 which is gripped between the first and second clamps 88, 91.

The apparatus 80 includes a displacement controller 96 connected to the first and second clamps 88, 91 for control of the respective longitudinal displacements thereof. The displacement controller 96 produces specific longitudinal displacements of the first and second clamps 88, 91 resulting in a corresponding longitudinal expansion of a specific amount in the portion of the PTFE tube 86 which is gripped between the first and second clamps. The displacement controller 96 may be adjustable to provide for variable longitudinal displacements of the first and second clamps 88, 91 to longitudinally expand by corresponding specific amounts the portion of the PTFE tube 86 which is gripped between the first and second clamps.

The displacement controller 96 may provide for control of the speed of the longitudinal displacement of the first and second clamps 88, 91 such that the longitudinal displacement produces a corresponding stretch rate of longitudinal expansion of the portion of the PTFE tube 86 which is gripped between the first and second clamps. The stretch rate is defined as the increase in the length of the portion of the PTFE tube 86 which is gripped between the first and second clamps 88, 91 divided by the corresponding time period during which the length is increased. The displacement controller 96 may be adjustable to provide for variable speeds of longitudinal displacement of the first and second clamps 88, 91 to longitudinally expand by corresponding specific stretch rates the portion of the PTFE tube 86 which is gripped between the first and second clamps.

In the alternative embodiment of apparatus 80 in which one of the clamps 88, 91 is fixed relative to the base 82, the displacement controller 96 is connected to the other of the clamps which may be longitudinally displaced to longitudinally expand the portion of the PTFE tube 86 which is gripped between the first and second clamps. The displacement controller 96 may thereby provide adjustable control of both the specific amount of the longitudinal expansion of the portion of the PTFE tube 86 which is gripped between the first and second clamps, and the stretch rate of the longitudinal expansion.

The apparatus 80 includes an energy source 98 mounted on the base 82 in proximity to the portion of the PTFE tube 86 which is gripped between the first and second clamps 88, 91 when the PTFE tube is supported by the support fixture 84. The energy source 98 is thermally coupled to the portion of the PTFE tube 86 between the first and second clamps 88, 91 to transfer heat to the portion of the PTFE tube. The energy source 98 is positioned relative to the PTFE tube 86 to enable the thermal coupling and resultant transfer of heat to the PTFE tube before and/or during the expansion thereof. The energy source 98 also provides for control of the timing of the transfer of heat to the PTFE tube 86 to provide for the transfer of heat before and/or during the expansion of the PTFE tube.

The apparatus 80 includes a temperature controller 100 connected to the energy source 98. The temperature controller 100 provides for control of the heat transferred from the energy source 98 to the portion of the PTFE tube 86 between the first and second clamps 88, 91 to control the temperature of the portion of the PTFE tube before and/or during the expansion thereof. The temperature controller 100 may be adjustable to provide for variation of the temperature of the portion of the PTFE tube 86 between the first and second clamps 88, 91 before and/or during the expansion of the PTFE tube.

The apparatus 80 includes a detector 102 having a sensor 104 for measuring a characteristic of the microstructure in the portion of the PTFE tube 86 which is gripped between the first and second clamps 88, 91. The detector 102 has an output device 106 connected to the sensor 104. The output device 106 generates a measurement signal which indicates the characteristic measured by the sensor 104.

The apparatus 80 further includes a comparator 108 connected to the output device 106. The comparator 108 receives the measurement signal from the output device 106 and compares the measurement signal to a reference, which indicates an acceptable measurement of the characteristic. The comparator 108 generates an acceptability signal if the measurement signal is the same as or sufficiently close to the reference. The comparator 108 generates a non-acceptability signal if the measurement signal is neither the same as nor sufficiently close to the reference.

The sensor 104 may be of various types for measuring various characteristics of the microstructure in the portion of the PTFE tube 86 which is gripped between the first and second clamps 88, 91. For example, the sensor 104 may be able to measure the IND in the portion of the PTFE tube 86 after the longitudinal expansion thereof. The IND is the distance between adjacent nodes of the node and fibril microstructure which results from the longitudinal expansion of the portion of the PTFE tube 86 which is gripped between the first and second clamps 88, 91.

Alternatively, the sensor 104 may be able to measure the permeation rate in the portion of the PTFE tube 86 after the longitudinal expansion thereof. The permeation rate is the speed with which a gas flows through a wall of the portion of the PTFE tube 86. The gas flow results from pores in the portion of the PTFE tube 86.

Alternatively further, the sensor 104 may be able to measure the strength, such as the tensile strength or circumferential hoop strength, of the portion of the PTFE tube 86 after the longitudinal expansion thereof.

The apparatus 80 may be used to longitudinally expand additional longitudinal portions of the PTFE tube 86 by moving the first and second clamps 88, 91 to other specific longitudinal positions along the PTFE tube and operating the apparatus as described in the foregoing. The apparatus 80 may be operated to longitudinally expand at least two longitudinal portions of the PTFE tube 86. Where two such longitudinal portions of the PTFE tube 86 are expanded using the apparatus 80, one end of each such portion may be coincident with or adjacent to one of the ends of the PTFE tube 86. When using the apparatus 80 to perform such expansions, either the first or second positions 90, 92 may be coincident with or adjacent to one of the ends of the PTFE tube 86.

The entire disclosures of the following U.S. Patent Applications, each of which is being filed in the USPTO on even date herewith, are hereby incorporated by reference herein:

Title: "Sintered Ring Supported Vascular Graft"; Inventors: Jamie Henderson and Dennis Kujawski; application Ser. No. 11/026,748; and Title: "Sintered Structures for Vascular Graft"; Inventor: Jamie Henderson; application Ser. No. 11/026,609.

While the invention has been described by reference to certain preferred embodiments, it should be understood that numerous changes could be made within the spirit and scope of the inventive concept described. Accordingly, it is intended that the invention not be limited to the disclosed embodi-

What is claimed is:

1. A differentially expanded vascular graft for implantation within a body, said vascular graft comprising:

a PTFE tube formed of a homogenous material, said PTFE tube having a plurality of surfaces including a luminal surface and an abluminal surface and a wall extending therebetween, at least one of said plurality of surfaces having a longitudinal first portion which has been longitudinally expanded and a longitudinal second portion which has been longitudinally expanded, said first and second portions have respective microstructures which are different from one another, said first and second portions having respective longitudinal positions relative to said PTFE tube wherein said respective longitudinal positions are different from one another, said first portion being unsintered and said second portion being sintered to lock the microstructure thereof.

2. A differentially expanded vascular graft according to claim 1, wherein said microstructures of said first and second portions are different before the respective longitudinal expansions thereof.

3. A differentially expanded vascular graft according to claim 2, wherein the respective longitudinal expansions of said first and second portions are the same.

4. A differentially expanded vascular graft according to claim 1, wherein said first and second portions have substantially different lengths after said respective first and second expansions.

* * * * *